United States Patent
Detweiler et al.

(10) Patent No.: US 9,549,499 B2
(45) Date of Patent: Jan. 24, 2017

(54) SOLID CARRIER SPRAYER APPARATUS AND METHODS OF USING SAME

(71) Applicant: Board of Trustees of Michigan State University, East Lansing, MI (US)

(72) Inventors: A. Ronald Detweiler, Okemos, MI (US); Gary Zehr, St. Johns, MI (US); Joseph Vargas, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 14/101,723

(22) Filed: Dec. 10, 2013

(65) Prior Publication Data

US 2014/0097264 A1    Apr. 10, 2014

Related U.S. Application Data

(63) Continuation-in-part of application No. 13/472,213, filed on May 15, 2012, now Pat. No. 8,623,111, which
(Continued)

(51) Int. Cl.
*A01C 15/00* (2006.01)
*A01C 21/00* (2006.01)
(Continued)

(52) U.S. Cl.
CPC ............ *A01C 15/005* (2013.01); *A01C 15/007* (2013.01); *A01C 21/00* (2013.01); *A01C 21/002* (2013.01);
(Continued)

(58) Field of Classification Search
CPC ..... A01C 15/005; A01C 15/00; A01C 15/007; A01C 15/006; A01C 21/00; A01C 21/002; A01M 11/00; A01N 25/00; A01N 25/08; C05D 9/00; C05F 11/02; C05F 11/00
See application file for complete search history.

(56) References Cited

U.S. PATENT DOCUMENTS 1,903,874 A    4/1933   Mills et al.
2,574,503 A  * 11/1951  Simpson .................... B01J 8/12
                                                      196/132
(Continued)

FOREIGN PATENT DOCUMENTS

WO    2009/064342 A1    5/2009

OTHER PUBLICATIONS

"Mixture of Fungicides and Insecticides", Research Disclosure No. 338093, Jun. 1992, pp. 1-10.
(Continued)

*Primary Examiner* — Christopher J Novosad

(57) ABSTRACT

A solid carrier sprayer apparatus, including a solid carrier container, a liquid container, a solid carrier spreading apparatus, and a liquid application apparatus is provided. The solid carrier spreading apparatus can be coupled to receive solid carrier from the solid carrier container, and is configured to drop the received solid carrier substantially evenly over an area of ground. The liquid application apparatus can be coupled to receive liquid from the liquid container, and is configured to spray received liquid substantially evenly over the received solid carrier, such that the liquid is sprayed substantially evenly over the received solid carrier before the solid carrier is dropped substantially evenly over the area of ground. Methods of using a solid carrier sprayer apparatus are also discussed.

46 Claims, 6 Drawing Sheets

Figure 1:
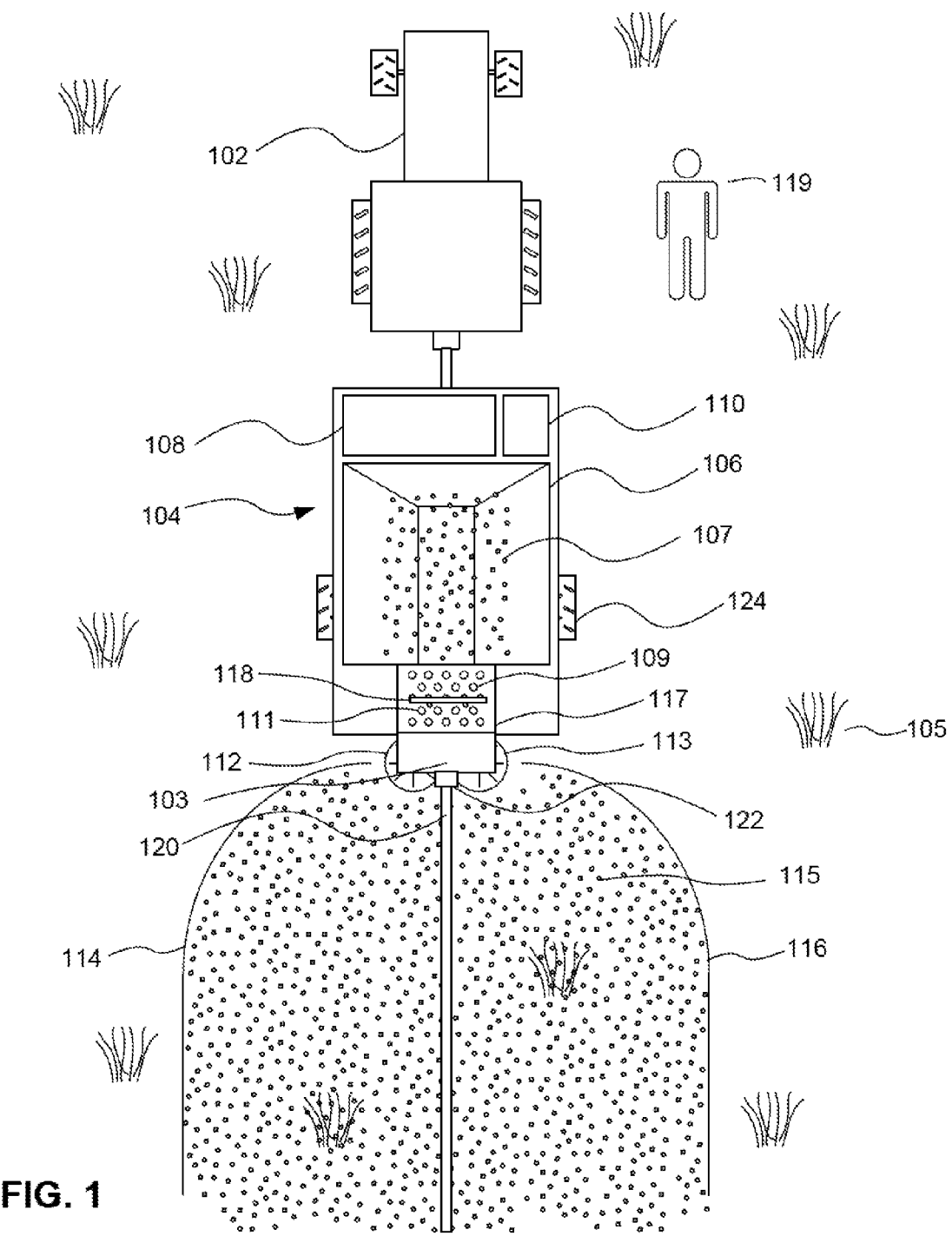

Related U.S. Application Data is a continuation of application No. 12/288,194, filed on Oct. 17, 2008, now Pat. No. 8,202,343, application No. 14/101,723, which is a continuation-in-part of application No. 12/288,188, filed on Oct. 17, 2008, now abandoned.

(60) Provisional application No. 61/002,898, filed on Nov. 13, 2007.

(51) Int. Cl.
| | |
|---|---|
| *A01M 11/00* | (2006.01) |
| *A01N 25/00* | (2006.01) |
| *A01N 25/08* | (2006.01) |
| *C05D 9/00* | (2006.01) |
| *C05F 11/02* | (2006.01) |

(52) U.S. Cl.
CPC ............. *A01M 11/00* (2013.01); *A01N 25/00* (2013.01); *A01N 25/08* (2013.01); *C05D 9/00* (2013.01); *C05F 11/02* (2013.01)

(56) References Cited

U.S. PATENT DOCUMENTS

| | | | |
|---|---|---|---|
| 3,923,492 A | 12/1975 | Collins et al. | |
| 4,712,919 A | 12/1987 | Bouldin | |
| 4,886,208 A | 12/1989 | Strand | |
| 5,251,656 A * | 10/1993 | Sexton, Sr. | B01F 1/0027 137/1 |
| 5,437,335 A | 8/1995 | Hines, Sr. | |
| 5,860,604 A | 1/1999 | Kooiker | |
| 6,336,600 B1 | 1/2002 | Jessen | |
| 7,370,818 B2 | 5/2008 | Ward et al. | |
| 8,202,343 B2 | 6/2012 | Detweiler et al. | |
| 8,623,111 B2 | 1/2014 | Detweiler et al. | |
| 2004/0023809 A1 | 2/2004 | Wertz et al. | |
| 2004/0077500 A1 | 4/2004 | Sakata et al. | |
| 2006/0006256 A1 | 1/2006 | Smith et al. | |
| 2008/0064663 A1* | 3/2008 | Gaytan | A01N 57/28 514/114 |
| 2009/0181849 A1 | 7/2009 | Detweiler et al. | |
| 2012/0234219 A1 | 9/2012 | Detweiler et al. | |

OTHER PUBLICATIONS

"Sand", Available at: https://en.wikipedia.org/wiki/Sand, Retrieved on Apr. 16, 2014, pp. 1-2.
Final Office Action received for U.S. Appl. No. 12/288,188, mailed on Jan. 25, 2012, 15 pages.
Non Final Office Action received for U.S. Appl. No. 12/288,188, mailed on Mar. 10, 2014, 22 pages.
Non Final Office Action received for U.S. Appl. No. 12/288,188, mailed on May 11, 2011, 27 pages.
Final Office Action received for U.S. Appl. No. 12/288,193, mailed on Mar. 3, 2011, 7 pages.
Non Final Office Action received for U.S. Appl. No. 12/288,193, mailed on Jun. 10, 2010, 11 pages.
Notice of Allowance received for U.S. Appl. No. 12/288,193, mailed on May 20, 2011, 5 pages.
Non Final Office Action received for U.S. Appl. No. 12/288,194, mailed on Sep. 23, 2010, 8 pages.
Notice of Allowance received for U.S. Appl. No. 12/288,194, mailed on Feb. 22, 2012, 7 pages.
Final Office Action received for U.S. Appl. No. 13/472,213, mailed on May 17, 2013, 15 pages.
Non Final Office Action received for U.S. Appl. No. 13/472,213, mailed on Dec. 14, 2012, 10 pages.
Notice of Allowance received for U.S. Appl. No. 13/472,213, mailed on Aug. 27, 2013, 6 pages.
Handreck et al., "Managing Turf Soils", Chapter 19, Growing Media for Ornamental Plants and Turf, Third Edition, 2002, pp. 247-275.
International Preliminary Report on Patentability received for PCT Patent Application No. PCT/US2008/011912, issued on May 18, 2010, 9 pages.
International Search Report and Written Opinion received for PCT Patent Application No. PCT/US2008/011912, mailed on Dec. 29, 2008, 9 pages.
Sanders et al., "Uptake, Translocation, and Efficacy of Triadimefon in Control of Turfgrass Pathogens", Disease Control and Pest Management, vol. 68, Oct. 1978, pp. 1482-1487.
White, "Techno Revolution: Topdressing Trends", Superintendent Magazine—Science, Technology and New Products for Golf Course Superintendent, Web page available at: http://www.superintendentmagazine.com/article.aspx?articleId=9236, Mar. 2013, 6 pages.

* cited by examiner

SOLID CARRIER SPRAYER APPARATUS AND METHODS OF USING SAME

CROSS-REFERENCE TO RELATED APPLICATIONS

This application is a continuation-in-part of U.S. patent application Ser. No. 13/472,213 filed on May 15, 2012, now allowed, which application is a continuation of U.S. patent application Ser. No. 12/288,194, filed on Nov. 13, 2008, which issued as U.S. Pat. No. 8,202,343 on Jun. 19, 2012, which application claims priority to U.S. Provisional Patent Application Ser. No. 61/002,898, filed on Nov. 13, 2007, all of which are hereby incorporated by reference herein in their entireties. This application is also a continuation-in-part of U.S. patent application Ser. No. 12/288,188, filed on Oct. 7, 2008, which is hereby incorporated by reference in its entirety, which application also claims priority to U.S. Provisional Patent Application Ser. No. 61/002,898, filed on Nov. 13, 2007.

BACKGROUND

Turf grasses, such as are commonly found on golf courses and other athletic fields, typically require extensive maintenance to ensure high quality playing conditions. Such maintenance includes application of top dressing materials such as sand or organic matter, as well as application of treatments such as fungicides and fertilizer. However, each application results in undesirable compaction of the soil as machinery drives across the turf grass, as well as disruption in use of heavily used turf areas such as golf courses.

SUMMARY

The embodiments described herein provide various configurations of a solid carrier sprayer apparatus, such as a sand sprayer apparatus, and methods related thereto. In one embodiment, a sand sprayer apparatus includes a sand container, a liquid container, a sand spreading apparatus, and a liquid application apparatus. The sand spreading apparatus can be coupled to receive sand from the sand container, and can further be configured to drop the received sand substantially evenly over an area of ground. In one embodiment, the liquid application apparatus is coupled to receive liquid from the liquid container, and is configured to spray received liquid substantially evenly over the received sand, such that the liquid is sprayed substantially evenly over the received sand before the sand is dropped substantially evenly over turfgrass.

In one embodiment, the sand sprayer apparatus further comprises a foam marker apparatus, configured to deposit a visible foam trail marking the dropped sand.

In one embodiment, the liquid application apparatus comprises two or more spray nozzles, and in a further embodiment are separately controllable to provide coverage to a portion or all of the sand being spread via the sand spreading apparatus. The sand may comprise material selected from silica, cristobolite, flint, chert, opal, chalcedony, and mixtures thereof. In one embodiment, the liquid application apparatus comprises two or more nozzles on a turret, such as nozzles that have different flow rates or that may be easily switched in for a clogged nozzle by rotating the turret.

In one embodiment, the liquid container comprises a mixer operable to keep liquid in the container in a mixed state. The mixer comprises, in various embodiments, a mechanical mixer, such as one or more paddles, propellers, screws, and/or other such devices. In various embodiments, the mixer can further comprise one or more liquid nozzles and/or jets that are configured to recirculate liquid in the container, such as via an external pump. The external pump can include any suitable pump known in the art capable of performing the intended function. In one embodiment, the liquid container comprises a conical portion that narrows near its bottom, reducing surface area and corners on the bottom of the liquid container to reduce settling. Various embodiments include containers of any suitable shape, such as square liquid containers, barrel liquid containers, and the like, further including liquid container configurations configured to include a sump (i.e., container). These liquid containers may further comprise other components, such as an internal sump (pump) mixer operable to keep liquid in the containers in a mixed state.

In one embodiment, the sand sprayer apparatus further comprises a second, smaller liquid container, such as a liquid container having a size that is less than half, a third, or a quarter, or any range therebetween, of the main liquid container. The smaller liquid container can, in various embodiments, be selectable for spraying sand, such as for a small batch that will consume as much liquid material as will fit in the smaller liquid container or less. In one embodiment, the smaller liquid container is configurable for other purposes, such as for use as a rinse tank to rinse the main liquid container, hoses, nozzles, and the like with fresh water.

The various embodiments described herein provide an improved sand sprayer apparatus that is operable to spray liquid materials onto sand and/or other solids that are spread over turfgrass to reduce the number of application passes that must be made. This results in a reduction in compaction of the turfgrass, and reduces the time and labor that are spent on turf maintenance. This also reduces downtime on heavily used turfgrass, such as golf courses and other such facilities.

BRIEF DESCRIPTION OF THE FIGURES

FIG. 1 shows an example sand spreader apparatus, according to an embodiment.

FIG. 2 shows an example of a sand sprayer apparatus with a center foam marker, according to an embodiment.

FIG. 3 shows an example of a sand sprayer apparatus with a side foam marker, according to an embodiment.

FIGS. 4A and 4B illustrate liquid containers having agitators configured to keep liquids in a mixed state, according to various embodiments.

FIG. 5 shows a plumbing configuration for a sand sprayer having recirculation nozzles and two liquid containers, according to an embodiment.

FIG. 6 shows a sprayer apparatus having adjustable nozzle turrets, according to an embodiment.

DETAILED DESCRIPTION OF THE EMBODIMENTS

In the following detailed description, reference is made to the accompanying drawings that form a part hereof and in which are shown, by way of illustration, specific embodiments in which the invention may be practiced. These embodiments are described in sufficient detail to enable those skilled in the art to practice the invention. Other embodiments may be utilized, and structural, logical, mechanical, electrical, and other changes may be made.

Turfgrass maintenance typically includes application of a variety of top dressing materials, as well as application of liquid treatments such as fungicides and fertilizer. However, each application (i.e., trip or pass with the application machinery) results in undesirable compaction of the turf as application machinery drives across the turfgrass, as well as disruption in use of heavily used turf areas, such as golf courses. Because reduction in the amount of time and labor spent applying turfgrass treatment is desirable, as is reducing compaction of the turfgrass, it is desirable to reduce the number of vehicle passes used to apply material to turfgrass.

Modern top dressing includes application of a variety of materials to the turfgrass, which materials are deposited in a thin layer of material over the turf surface. Top dressing materials include, but are not limited to, fertilizer, sand, organic matter, soil, turfgrass seed, and other such materials. Various topdressings can limit thatch, level and smooth the turf grass surface, and improve the drainage, organic matter composition, or other qualities of the turfgrass. Application of top dressing materials can be performed in a variety of ways, including by hand (such as with a landscaping rake), with a mechanical drop spreader that drops the material substantially uniformly onto the turfgrass, or with a mechanical broadcast spreader that broadcasts or distributes the top dressing material outward from a spinner.

Application of liquid turfgrass treatments such as fungicides, insecticides, and herbicides and/or weed killers is typically performed with different equipment, designed to distribute and apply liquid material rather than solid matter. Although some fertilizers are provided as solids and may be distributed in a manner similar to top dressing distribution, many fertilizers are liquid, and are therefore also sprayed onto turfgrass. Sprayers typically used for applications of liquids, such as fertilizers and fungicides include an array of spray nozzles attached to a vehicle, such as a bar having attached spray nozzles extending perpendicular to the vehicle's direction of travel, coupled to a liquid container.

However, such sprayers often allow sprayed material to drift somewhat, as the height of the nozzle array above the turfgrass must be sufficiently high to ensure even coverage to the turfgrass and to avoid contact with uneven ground. Furthermore, hauling large amounts of liquid in a sprayer vehicle results in a heavy sprayer apparatus that compacts the soil supporting the turfgrass, just as hauling large amounts of topdressing for distribution results in turfgrass soil compaction. It is therefore desirable to ensure even distribution of liquid turfgrass treatments, and to reduce the number of vehicle trips to apply material to turfgrass to reduce soil compaction, labor, and application time.

Various embodiments presented herein therefore utilize a combination spreader/sprayer apparatus, such as a sand sprayer configured to deposit sand comprising sand particles that are substantially evenly sprayed with liquid from a container using a sprayer to form sprayed sand while being conveyed before being deposited on turfgrass as deposited sand. This configuration eliminates the need to deposit sand and liquid separately, and reduces the amount of time and labor needed relative to configurations in which the sand and liquid are deposited separately. It also reduces turfgrass soil compaction, and provides more even application of the liquid than may sometimes be achieved using a conventional spray apparatus.

FIG. 1 shows an example solid carrier spreader apparatus, consistent with an embodiment. In this embodiment, a tractor 102 is configured to pull a solid carrier sprayer apparatus, e.g., the sand sprayer apparatus 104, configured in this embodiment as a trailer. In other embodiments, the sand sprayer apparatus 104 may be configured as a standalone vehicle, such as on a truck bed or vehicle frame, or is incorporated as a part of another vehicle or trailer.

The sand sprayer apparatus 104 shown in FIG. 1 comprises a sand hopper 106, which is a container for holding contained sand 107 to be spread over one or more portions of a surface (e.g., a portion of turf grass 105) as deposited sand 115. In the embodiment shown in FIG. 1, the sand sprayer apparatus 104 also includes a large liquid container (i.e., tank) 108 and a small liquid container 110. The large liquid container 108 can hold a variety of liquid materials to be spread over the one or more portions of a surface (e.g. turfgrass 105), such as fertilizer, fungicide, herbicide, insecticide, and the like. The small liquid container 110 can similarly hold liquid to be spread over the turfgrass 105, or, in another embodiment, can additionally or alternatively be used to hold fresh water to flush the large liquid container 108, hoses, spray nozzles, and/or other components.

In the embodiment shown in FIG. 1, the sand sprayer apparatus 104 further comprises a sand conveyor 117 that is operable to move contained sand 107 from the sand hopper 106 along the conveyer as conveyed sand 109. The conveyed sand 109 is sprayed with liquid using liquid sprayer 118 to form sprayed sand 111, which is conveyed to a sand spreader apparatus 103 where it is then deposited on the turf grass as deposited sand 115 in two contiguous sections 114 and 116. In other embodiments, other sand conveyance apparatus are employed, such as an auger or screw. In various embodiments, the conveyed sand is sprayed as it is being transferred to a conveyance apparatus such as an auger, while it is being conveyed, as it is being transferred from the conveyance apparatus to a spreader apparatus, and/or as it is being distributed from the spreader apparatus.

In the embodiment of FIG. 1, the sand spreader apparatus 103 comprises a sand spinner or spinning disc 112 and 113 used to toss or fling sand in a substantially even thickness or area density in a pattern behind the sand sprayer apparatus 104. In other embodiments, the sand spreader apparatus 103 comprises a drop spreader configured to drop sand in an even path behind the spreader or comprises another spreading mechanism. Although spinner and drop spreaders are well-known in the art, a variety of other spreader configurations may be used in various embodiments.

In the embodiment shown in FIG. 1, the sprayed sand 111 is distributed onto the turf grass 105 using separate sand spinners 112 and 113, on opposing sides, e.g., the left side and right side of the sand sprayer apparatus 104. The sprayed sand 111 is deposited as deposited sand 115, comprising the two contiguous sections 114, 116, namely a "left" section (e.g., half) 114 and a "right" section (e.g., half 116), each section being laid down by the sand spinner 112 or 113 on the corresponding side of the sand sprayer apparatus 104. In one embodiment, each half (114, 116) of the deposited sand 115 is substantially similar in size and shape.

The liquid sprayer 118 of the sand sprayer apparatus 104 can be coupled to the large container 108 and/or the small container 110, and configured to receive liquid from the large container 108 and/or the small container 110. As discussed above, the received liquid is sprayed substantially evenly over the conveyed sand 109 on the sand conveyor 117 to form sprayed sand 111, which is thereafter spread substantially evenly over the turf grass 105 in two contiguous sections 114, 116, as deposited sand 115. This results in substantially even distribution of both the contained sand 107 from the sand hopper 106 and the received liquid. Because liquids sprayed over ground using traditional sprayer apparatus tend to drift in wind and volatize, the sand sprayer apparatus 104 further provides, in some applications, more even application and less volatization of the liquid than can be achieved using traditional spray apparatus.

In operation, a user or users 119 drives the tractor 102, i.e., moves the tractor 102 forward, towing the sand sprayer apparatus 104 behind it. As the tractor 102 moves forward, one of the users 119 can initiate operation of the sand sprayer 104 or pre-set desired parameters can be activated as described below, to cause the sand sprayer apparatus 104 to operate to extract contained sand 107 from the sand hopper 106 via the sand conveyor 117. The conveyed sand 109 is then sprayed with liquid from the liquid sprayer 118, to form sprayed sand 111 that is then delivered to the sand spreader apparatus 103. The sand spreader apparatus 103 distributes the sprayed sand 111 onto the turfgrass 105 as the tractor 102 and sand sprayer apparatus 104 drive forward, resulting in a path (i.e., two contiguous sections 114 and 116) of deposited sand 115 being deposited on the turf grass 105 behind the sand sprayer apparatus 104, as shown in FIG. 1.

The rate of sand deposited, the rate of liquid sprayed, and other such variables are controlled in some embodiments by pre-setting the desired parameter on the sand sprayer apparatus 104 before driving, and, in other embodiments, the user 119 controls one or more of these parameters from the tractor 102. In a more detailed embodiment, the sand conveyor 117, liquid sprayer 118, and sand spreader apparatus 103 operate based on the speed of the sand sprayer apparatus 104, such as by the rate of rotation of trailer wheels 124. In another embodiment, the amount of liquid sprayed per volume of sand is controlled by selection of various nozzles on the liquid sprayer 118, or by other means such as regulation of liquid pressure or number of nozzles used.

In some embodiments, an appropriate rate of sand spreading for a desired tractor speed is determined and an appropriate conveyor speed for the sand conveyor 117 is selected, and a desired rate of liquid application is determined and appropriate nozzles and/or liquid pressure are selected. In a further embodiment, a user 119 activates the sand sprayer apparatus 104 only after the user 119 has determined that the tractor 102 has reached a desired speed, resulting in the desired rate of sand and liquid application.

Some embodiments of sand sprayer apparatus 104 further comprise a foam marker apparatus 122 mounted at or near the center of the sand sprayer apparatus 104, such as under or near a hitch. The foam marker apparatus 122 is operable to deposit a foam track 120 on the ground, thus covering the center area of the two contiguous sections 114, 116 as they are being deposited to cause the two contiguous sections 114, 116 to appear instead as two separate sections of deposited sand 115, which, in this embodiment, are of substantially the same size and shape. In other embodiments, the foam marker apparatus 122 is located at another position along or to the side of the sand spreader apparatus 103, such as near the far left edge of left section 114 or near the far right edge of right section 116.

The foam in various embodiments comprises any material that will not harm the turf grass, but that remains visible for at least several minutes such that user 119 can see the path of deposited sand 115. In some embodiments, the foam comprises a gas, such as air, trapped in pockets of a liquid. Although traditional foams are formed by mechanically forming air or other gas pockets in a liquid foam material having a surfactant, a wide variety of suitable commercial foam products are available and are suitable for use with a foam marker as shown in FIG. 1.

Figure 2:
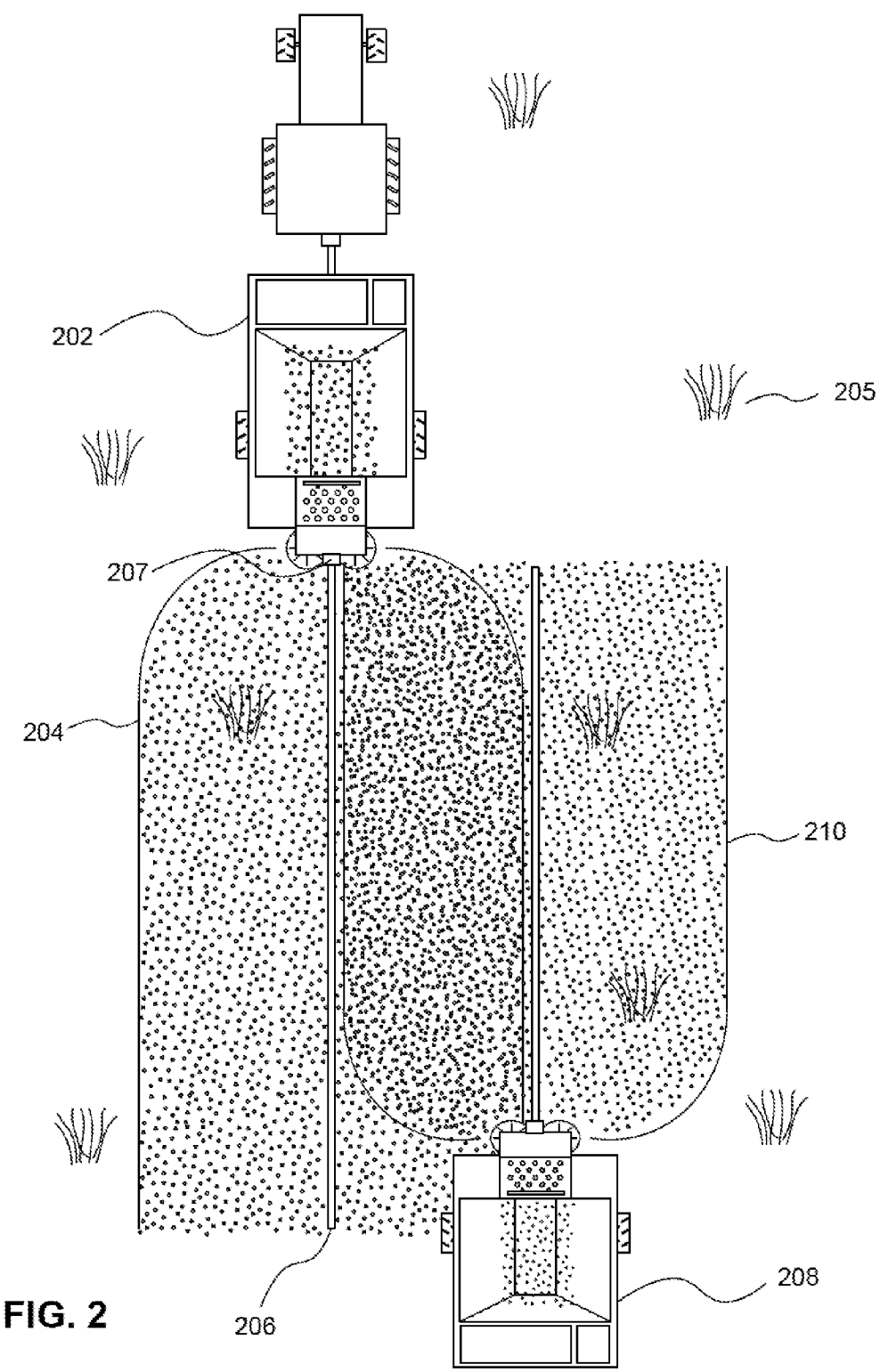

FIG. 2 shows an example of a sand sprayer apparatus with a center foam marker apparatus, consistent with an embodiment. Here, the sand sprayer apparatus is shown in two separate locations, with sand sprayer apparatus 202 (such as sand sprayer apparatus 104 of FIG. 1) in a first location and sand sprayer apparatus 208 in a second location. In this embodiment, the sand sprayer apparatus 202 has deposited a sand path 204 comprising deposited sand (such as the two contiguous sections 114, 116 of FIG. 1), together with foam which forms a center foam stripe 206 onto turf grass 205. In the embodiment shown, the center foam stripe 206 is deposited by foam marker apparatus 207, and serves to mark the approximate center of the sand path 204, such that when the sand sprayer apparatus 208 makes another pass over the turf grass 205, the user can align the right edge of the new sand path 210 with the foam stripe 206. This results in overlapping of the right side of each of sand path 204 and 210 as shown in FIG. 2, resulting in approximately double the application rate provided by a single pass.

In one embodiment, the sand sprayer apparatus makes additional passes, with each sand pattern overlapping the previous pattern by about 50%, resulting in an application rate approximately double that of a single pass across the turf grass. Although the percentage overlap may vary based on driver accuracy or by design, such as from about 40 to about 60% overlap or from about 45% to about 55% overlap, or any range there between, use of multiple overlapping passes near 50% (±1 to 5%) helps ensure that each area of turf grass 205 receives at least one pass of coverage. In other embodiments, the foam stripe 206 and sand path 204 can have different configurations, resulting in different coverage and/or overlap. In one such embodiment, approximately no overlap is desired between a first set of passes going west-east or east-west, but a second set of passes going north-south or south-north provides a second layer of sprayed sand, resulting in more even coverage than may be obtained with non-overlapping passes in a single direction.

In one embodiment, the sand sprayer apparatus 202 deposits a foam line 206 at one or more edges of sand pattern 204, such that on the next pass, the user can follow the foam line 206 such that the sand sprayer apparatus 208 can be centered over the foam line for approximately 50% (±1 to 5%) overlap, or can be adjacent to the edge foam line 206, such that the sprayed sand is deposited as deposited sand 210 up to the edge foam line 206 for no overlap.

Figure 3:
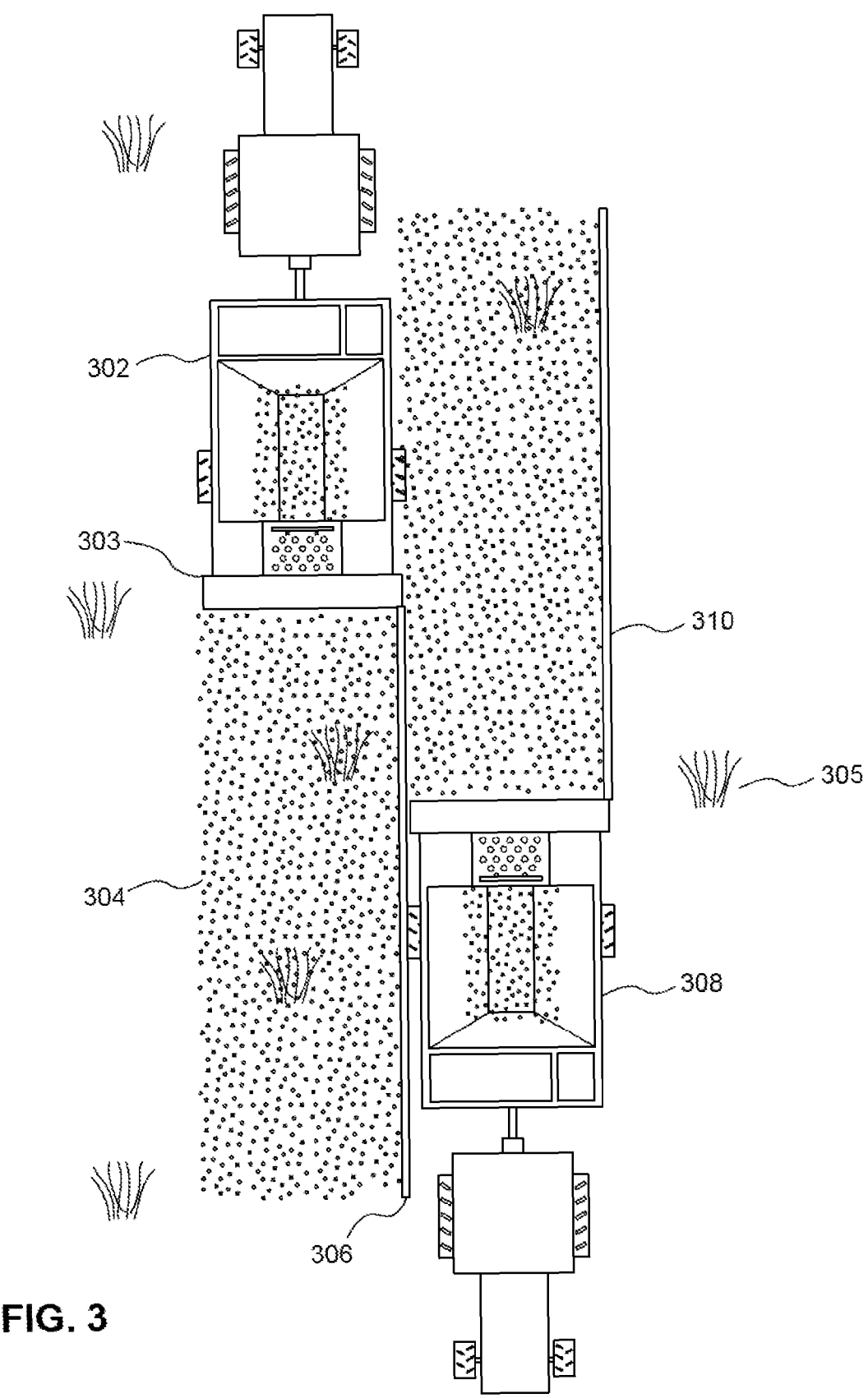

FIG. 3 shows an embodiment wherein a sand sprayer apparatus is again in two separate locations, with sand sprayer apparatus 302 in a first location and sand sprayer apparatus 308 in a second location. In this embodiment, the sand sprayer apparatus includes a side foam marker and a sand spreader 303 that drops sprayed sand, rather than sand which has been spun or tossed, resulting in a sprayed sand path 304 that is approximately as wide as the sand spreader 303. While this drop spreader configuration results in a narrower sprayed sand path 304 than is obtained with a spinner-based sand spreader as shown in FIG. 2, the sprayed sand can be deposited more evenly, more heavily and more precisely, as compared with a spinner-type spreader.

In this embodiment, the sand sprayer apparatus 302 deposits a sand path 304 with a foam line 306 near one edge of the sand path, rather than near the center of the sand path as in FIG. 2. This allows the sand sprayer apparatus 302 on the next pass (or another sand sprayer apparatus) as shown at 308 to follow the edge of the foam line 306, resulting in minimal overlap and precise coverage of the turf grass 305. In another embodiment, the sand sprayer apparatus 308 follows the center of the foam line 306 such that the sand sprayer apparatus 308 is approximately centered over foam line 306, resulting in approximately 50% (±1 to 5%) overlap on each pass. As the sand sprayer apparatus makes repeated passes to cover the turf area, all turf grass 305 except the outer half of the first and last passes will therefore receive approximately double the coverage they would receive with a single pass. Again, alternate coverage is possible, such as from about 40% to about 60% overlap.

Centered foam lines 206 as shown in FIG. 2 or edge foam lines 306 as shown in FIG. 3 may be utilized with any type of sand spreader apparatus, such as a drop spreader 303 or spinner spreaders as shown at 112 and 113 in FIG. 1, and in some embodiments are adjustable to match the sand distribution pattern of a spreader such as a spinner spreader. The foam lines may be used alone or in combination, such as marking both the left and right edges of a sand path, or marking the center and an edge of the sand path. Colored foams may also be used to identify different lines in some embodiments, and visible materials other than foam are used in other embodiments.

The foam material is in some embodiments provided as a liquid from a liquid container to a foam marker apparatus or foamer, such as from smaller liquid container 110 of FIG. 1 to a foam marker apparatus 122. In other embodiments, the smaller liquid container 110 contains fresh water that is used with another material to produce foam. The liquid containers in some embodiments are reconfigurable for various purposes such as this, and are operable to handle different types of liquids, including viscous liquids or liquids with suspended fine particles.

Figure 4A:
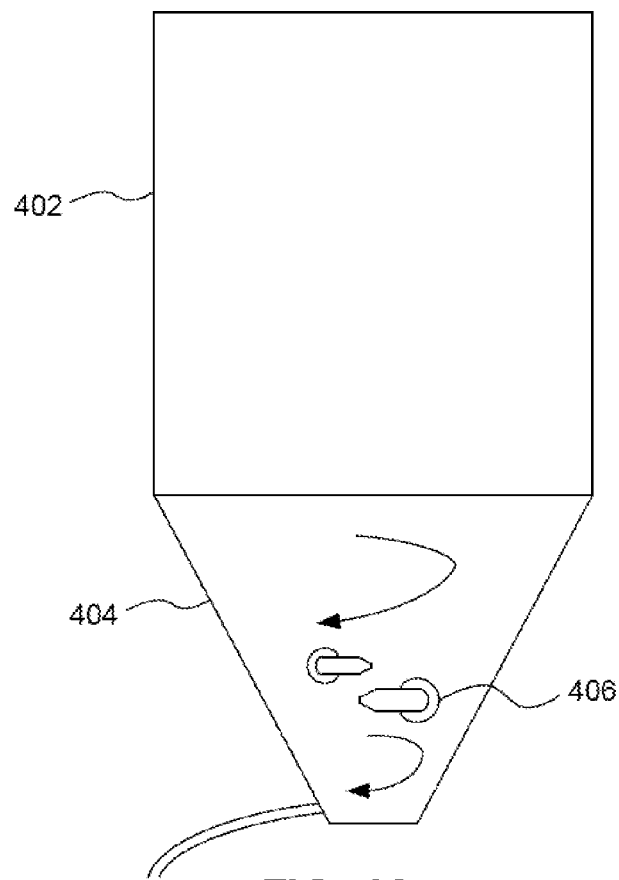
Figure 4B:
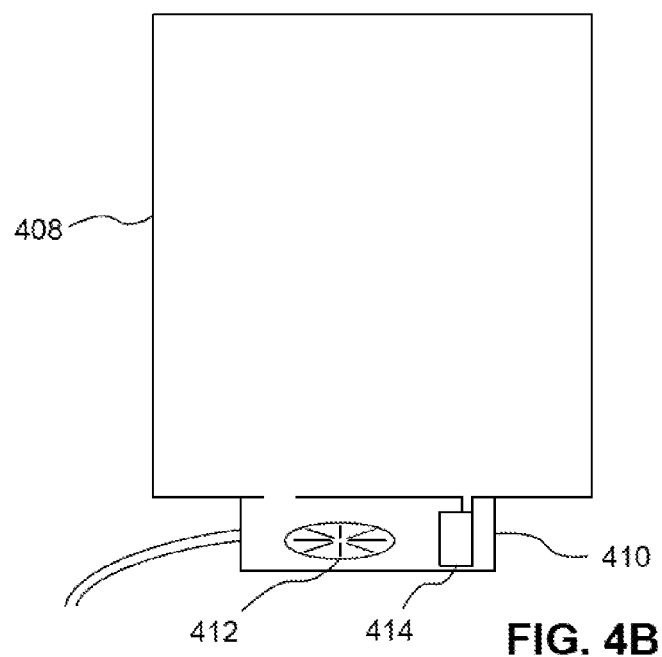

FIGS. 4A and 4B illustrate liquid containers having agitators configured to keep liquids in a mixed state, consistent with various embodiments. Referring to FIG. 4A, liquid container 402 in one embodiment is a conical liquid container, including a cylindrical top portion and a conical bottom portion 402 that is narrower near its bottom than at its top. The conical shape lacks the large flat bottom of a typical barrel-shaped or box-shaped liquid container, making it easier to drain and clean the liquid container without leaving settled material in the liquid container. The conical shape also helps keep liquids in the liquid container mixed, as it provides a minimal flat surface at the bottom onto which materials can settle.

The liquid container 402 in this embodiment further includes liquid nozzles or jets, 406 used to agitate the liquid in the bottom conical portion of the liquid container by recirculating the liquid. These features prevent viscous liquids or fine particles suspended in the liquid from settling to the bottom of the liquid container 402, keeping the liquid mixed. In other embodiments, other types of agitators may be used, such as a spinning disc, moving paddles, a submersible sump pump, and/or other such mechanisms.

In the embodiment illustrated in FIG. 4A, liquid is drawn near the bottom of the liquid container 402 and sprayed back into the liquid container 402 near its bottom, i.e., within a lower portion, such that the bottom portion of the liquid container remains agitated even with relatively little liquid left in the liquid container 402. In another embodiment, liquid can be drawn out the top of the conical portion of the liquid container and sprayed into the bottom of the conical portion 404, such that liquid sprayed into the bottom of the conical portion 404 is more dilute than any settled liquid at the bottom, keeping the liquid relatively mixed. In an alternate embodiment, liquid is taken from near the bottom of the conical portion 404 and sprayed back into the liquid container 402 higher up in the conical portion 404, such that more settled liquid from the bottom is mixed with more dilute liquid higher up in the liquid container 402. Methods such as these ensure that liquid in the liquid container 402 remains mixed, and that liquid at the bottom of the liquid container 402 does not become overly settled or concentrated.

FIG. 4B shows a box-shaped or rectangular-shaped liquid container 408, consistent with some embodiments. Here, a sump 410 is located at the bottom of the liquid container 408, and draws in liquid from the liquid container 408 through an opening linking the liquid container 408 and the sump 410. A spinning disc 412 with paddles or ridges agitates liquid in the sump, keeping liquid in the sump well-mixed and reducing fine particle settling in the sump. In another embodiment, a submersible sump pump 414 circulates liquid in the sump back through the liquid container 408, keeping liquid in the sump in a mixed state. In a further embodiment, an agitator such as a spinning disc, paddles, nozzles or jets, or other such mechanism is also present in the liquid container 408, which may or may not have a sump attached. In another embodiment, an agitator is present only in liquid container 408 and not in sump 410. Any such configuration will reduce concentration of liquid or settling of particles in the liquid container 408 and sump 410.

Liquid is drawn from the liquid containers and provided to sprayers using pipes, hoses, or other such fittings as shown in FIGS. 4A and 4B. In one embodiment, any suitable type of pump is employed to pressurize liquid drawn from the liquid container and sprayed through nozzles to coat sand before the sand is spread as shown in FIGS. 1-3. In some embodiments, the pump that draws liquid to be sprayed on the sand is also used to provide liquid to nozzles or jets as shown at 406 to reduce settling. A variety of such configurations are possible, and in various embodiments will be user-configurable to select recirculation, spraying sand, rinsing/flushing, or other operations driven by one or more such pumps.

Figure 5:
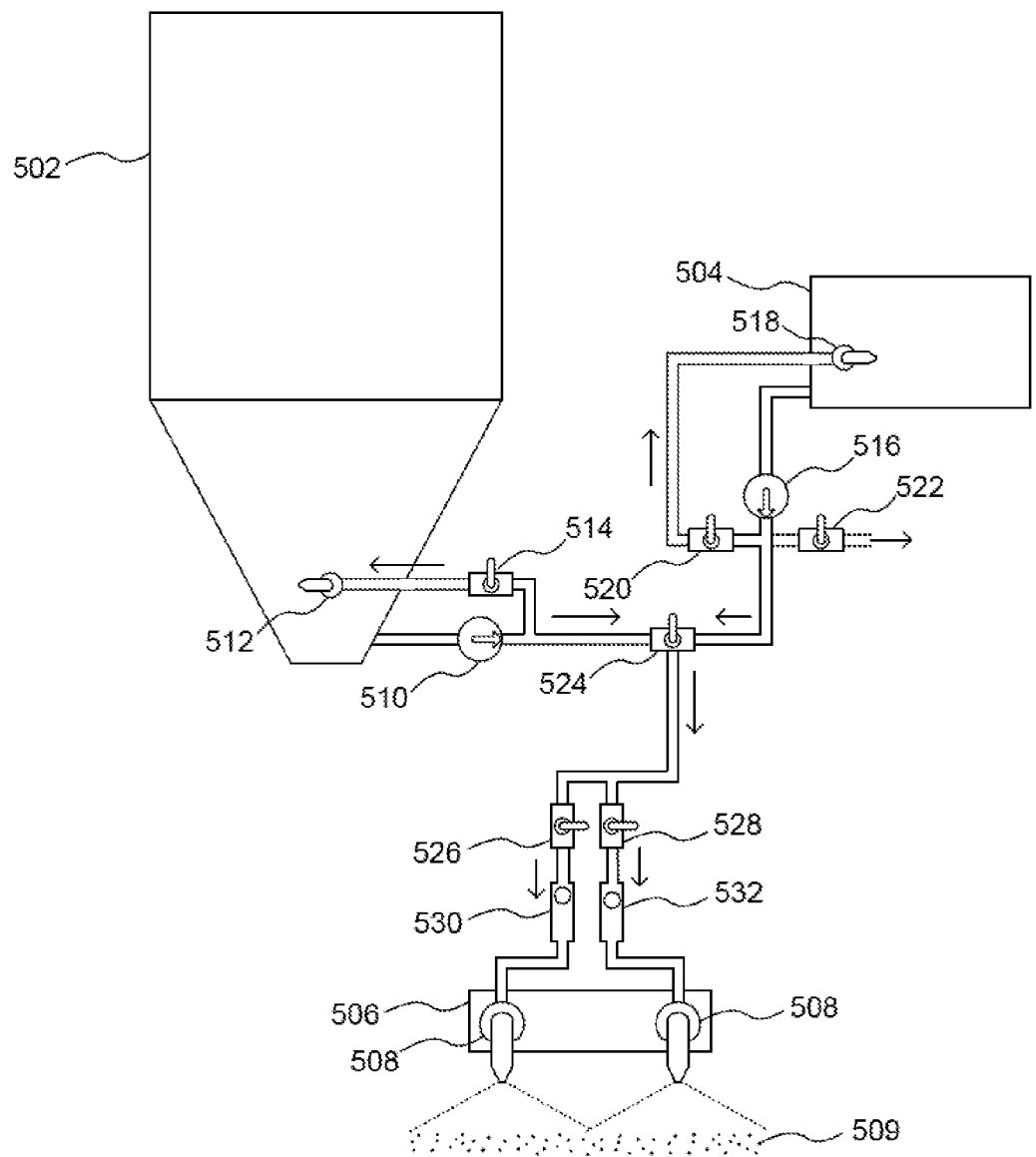

FIG. 5 shows a plumbing configuration for a sand sprayer apparatus having recirculation nozzles and two liquid containers, consistent with an embodiment. Here, a large liquid container 502 and a small liquid container 504 are coupled to a sprayer apparatus 506 having a pair of nozzles 508 operable to spray sand 509. The large liquid container 502 is coupled to a pump 510 that is operable to pump liquid from the large liquid container 502 to the nozzles, and to optionally pump liquid to the large liquid container agitator nozzle 512. Valve 514 controls whether the pump provides liquid to the agitator nozzle 512, and is in various embodiments a manual valve or an electric or solenoid-driven valve providing remote control of the valve configuration.

Small liquid container 504 is similarly coupled to a pump 516 that is operable to provide liquid from the small liquid container 504 to the sprayer apparatus 506, and optionally to provide a liquid to small liquid container agitator nozzle 518 through configuration of valve 520.

Embodiments having separate pumps for each liquid container further enable a user to agitate one liquid container without providing liquid to the nozzles while the other liquid container provides liquid to the nozzles, and enables the liquid containers to be used for different purposes. For example, the small liquid container 504 may be filled with fungicide and used for small applications of sprayed sand one day (such as applications where the small liquid container can hold all the liquid needed for a particular task), and may be filled with fresh water and used to flush or clean the large liquid container 502, piping, and sprayer apparatus 506 later on the same day or the next day. In one such embodiment, clean water from small liquid container 504 is pumped through pump 516 and a control valve 522 connecting the pumped liquid from smaller liquid container 504 to an optional hose fitting or the like, which is attached to a hose used to clean other sand sprayer parts.

In one embodiment, pumps 516 and 510 are replaced with a single pump, placed between liquid container selector valve 524 and valves 526/528. Such a configuration works well where recirculation nozzles are also selected by a valve coupled to 524, so that only liquid containers in use are recirculated. This configuration also works in applications where other agitation mechanisms are used or no agitation is used, such as with liquid containers having a mechanical agitator. However, when a single pump is used to drive the sprayer assembly 506 and agitator nozzles, the liquid container not selected is not agitated or available for other applications requiring pumped liquid.

Returning to the embodiment shown in FIG. 5, liquid container selector valve 524 selects which of large liquid container 502 and small liquid container 504 are used to provide liquid to the nozzle assembly 506. In an alternate embodiment, valve 524 enables coupling all three lines together, such as to use both liquid containers at the same time or to back flush the lines, valves, and nozzles.

Liquid from liquid container selector valve 524 flows to left nozzle selector valve 526 and right nozzle selector valve 528, which enable a user to selectively spray either the right half or left half of the sand 509, or both halves of the sand 509. Such a feature is particularly useful when using a sand spinner to apply sand near sensitive areas that are not to receive a sprayed solid carrier, such as sprayed sand, such as near sand traps on golf courses or near water. In some embodiments, the user is able to select which nozzles are active by actuating valves 526 and 528 while driving, such as by using remote levers or electronic or solenoid-operated valves.

A user can similarly monitor fluid flow through nozzles 508 by using electronic flow meters with remote readouts, but in some embodiments will use a more cost-effective in-line flow indicator such as visible ball apparatus 530 and 532. In one embodiment, these visible ball apparatus each include a floating ball that is either pushed downward, or otherwise moves in a clear tube or other transparent housing as a result of fluid flow through the apparatus, providing a visible indicator of fluid flow from a moderate distance such as from a tractor seat. In another embodiment, the visible ball is a sinking ball, and fluid flow from bottom of the visible ball apparatus to top drives the ball upward or otherwise moves the ball, visibly indicating fluid flow. One example of such a visible ball apparatus is the commercially available Redball™ spray monitor.

Visible ball flow indicators, such as the ones described and shown herein, simplify the sand sprayer apparatus and reduce cost relative to electronic flow indicators, while still providing a visible indication of the rate of flow of liquids through each visible ball indicator. They enable a user to quickly observe irregular flow or stoppages, such as a failed pump 510, an empty liquid container 502, or a clogged nozzle 508. The user can then promptly remedy the problem by performing appropriate actions, such as replacing a clogged nozzle, and can easily observe where or when such a liquid flow problem occurs so that the problem can be promptly corrected and accurate turfgrass coverage can be maintained.

Figure 6:
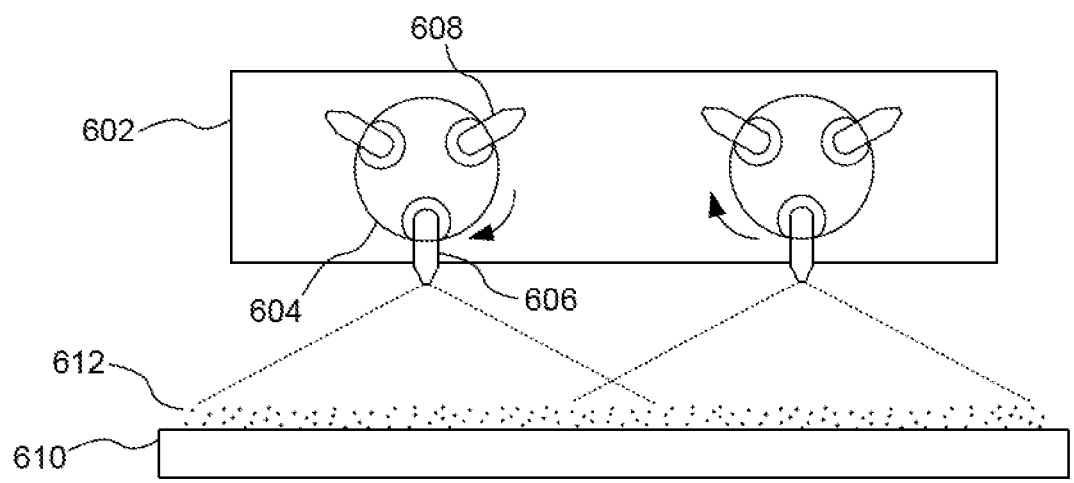

FIG. 6 shows a sprayer apparatus having adjustable nozzle turrets, consistent with an embodiment. Here, a sand sprayer apparatus 602, such as the sand sprayer apparatus 506 of FIG. 5 or 118 of FIG. 1, comprises at least one turret 604 that has two or more nozzles 606 and 608. The turret is adjustable so that one of the two or more nozzles is configured to spray toward conveyor 610, substantially evenly covering a layer of sand 612 received from a sand hopper for spreading.

In operation, liquid from a liquid container is provided to one or more turrets 604, such as through a pump or by gravity. The turrets in the embodiment of FIG. 6 are spaced on the sprayer apparatus 602 to provide substantially even coverage of conveyor 610 and sand 612, resulting in a relatively consistent amount of sprayed liquid per volume of sand. Substantially even turf grass distribution of sand from a sand spreader apparatus therefore also provides relatively even turf grass distribution of the liquid sprayed on the sand.

Although the turrets 604 here are shown as rotating turrets having three different configurations, turrets having two, four, or other numbers of configurations or nozzles are also used in other embodiments. Similarly, although the turrets shown are configured such that the nozzles pointing down such as nozzle 606 are the active nozzles on each turret, other configurations and nozzle orientations are used in other embodiments.

Should a nozzle such as nozzle 606 clog during sprayer operation, the turret 604 can be rotated to move nozzle 608 into the downward position, making nozzle 608 the active spray nozzle on that turret. This enables a sand sprayer apparatus to be easily reconfigured after a nozzle becomes clogged, so that sand spraying can continue without stopping for removal, replacement, or cleaning the clogged nozzle.

In another embodiment, nozzles on a turret such as nozzles 606 and 608 on turret 604 are different nozzles, such as nozzles having different flow rates. For example, turret 604 may have nozzles that spray 0.25, 0.5, and 1 gallon per minute at a specified pressure, and the sand sprayer operator selects the appropriate nozzle for a particular liquid to be sprayed on the sand to achieve the desired application rate.

Turrets having nozzles with different flow rates are particularly useful in environments where the same sand sprayer apparatus is used to apply different materials to sand, such as fungicides on one application and insecticides on a subsequent application. A groundskeeper may similarly desire to apply different amounts of sand or other solid material on top of turf grass, changing the amount of liquid that should be applied per volume of sand to achieve the same liquid coverage per turf grass area.

For example, a solid carrier, such as sand, may be sprayed with a liquid such as any type of humate (e.g., humic acid), herbicide (e.g., dicamba), insecticide (e.g., Merit®), plant growth regulator (e.g., trinexapac-ethyl), supplement (e.g., micronutrients, plant extracts), oils (e.g. mineral oil), a nematicide, and/or soil wetting agent (e.g., Cascade®). Similarly, a solid insecticide or fertilizer may be sprayed with an antifungal, a solid supplement may be sprayed with a growth regulator or humate, and other combinations of solids and liquids may be combined in the sand sprayer by spraying a solid with a liquid before spreading the solid. Many other examples of suitable application materials are found in the incorporated references, such as in U.S. Pat. No. 8,202,343 at col. 16-col. 64, and in the definitions at col. 5-col. 15.

Some experimental evidence suggests that the systemic (root and foliar absorbed) fungicides work particularly well when applied as sprayed-on sand, while the contact, surface protectant, non-systemic or limited systemic fungicides also work when applied as sprayed-on sand but may require higher application rates than if sprayed directly on turf grass. Because some insecticides and herbicides also work through surface contact with foliage, they may similarly require higher application rates when sprayed on deposited sand.

While not wishing to be bound by this proposed theory, this result may occur because there is less complete foliar coverage with sand-based applications than with direct spraying, such that sand-based active ingredients that rely on foliar absorption or coverage will require greater application rates when spread with sand. Examples of such foliar absorption or coverage materials include some fungicides, insecticides, and herbicides. Other sand-based active ingredients that are easily absorbed through the roots, such as many fertilizers, systemic fungicides and herbicides, and other such systemic materials, are also expected to work particularly well with the embodiments described herein, with effectiveness similar to direct spraying. Active ingredients that are primarily soil-active, such as soil wetting agents, are also expected to work well, with effectiveness similar to direct spraying.

Spraying such materials onto sand or other solids that are spread over turfgrass reduces the number of application trips that must be made. This results in a reduction in compaction of soil supporting the turfgrass, and reduces the time and labor that are spent on turf maintenance. This also reduces downtime on heavily used turfgrass, such as golf courses and other such facilities.

Although specific embodiments have been illustrated and described herein, any arrangement that achieve the same purpose, structure, or function may be substituted for the specific embodiments shown. For example, although the solid carrier sprayer apparatus has been described as a sand sprayer apparatus, other solid carriers are possible, including, but not limited to, a solid carrier which comprises a majority of weight sand and/or can otherwise contain peat, organic matter, soil, or mixtures thereof. This application is intended to cover any adaptations or variations of the embodiments of the invention described herein, and these and other embodiments are within the scope of the following claims and their equivalents.

What is claimed is:

1. A solid carrier sprayer apparatus, comprising:
   a solid carrier container;
   a liquid container;
   a solid carrier spreading apparatus coupled to the solid carrier container and configured to distribute a solid carrier received from the solid carrier container over an area of ground; and
   a liquid application apparatus comprising one or more spray nozzles coupled to the liquid container and configured to spray a liquid received from the liquid container over the received solid carrier, such that the liquid is sprayed over the received solid carrier before the solid carrier is distributed over the area of ground, wherein the liquid is selected from a humate, fertilizer, fungicide, antifungal, nematicide, weed killer, plant growth regulator, supplement, oil, soil wetting agent, herbicide, and combinations thereof, and the solid carrier is selected from sand, peat, organic matter, soil, and combinations thereof.

2. The solid carrier sprayer apparatus of claim 1 comprising a sand sprayer apparatus, wherein said spray nozzles comprise two or more spray nozzles coupled to user controls and configured to spray a selectable portion of the received solid carrier with the liquid.

3. The solid carrier sprayer apparatus of claim 1, wherein the solid carrier has first and second portions and the user controls are configured to spray the first portion, the second portion, or substantially all the received solid carrier with the liquid.

4. The solid carrier sprayer apparatus of claim 3, wherein the first and second portions comprise substantially equal portions.

5. The solid carrier sprayer apparatus of claim 1, further comprising one or more turrets, each of said turrets containing two or more turret spray nozzles, said turrets optionally separately operable and configured to selectively couple with a particular turret spray nozzle to receive the liquid.

6. The solid carrier sprayer apparatus of claim 5, wherein at least two of said turret spray nozzles have different rates of flow at a same received liquid pressure.

7. The solid carrier spray apparatus of claim 6 wherein a user can switch from a clogged nozzle to a replacement nozzle by rotating the turret.

8. The solid carrier sprayer apparatus of claim 5, wherein said turret spray nozzles have a substantially same rate of flow at the same received liquid pressure.

9. The solid carrier spray apparatus of claim 8 wherein a user can switch from a clogged nozzle to a replacement nozzle by rotating the turret.

10. The solid carrier sprayer apparatus of claim 1, further comprising at least one in-line flow indicator coupled between the liquid container and the liquid application apparatus and configured to indicate flow of the liquid.

11. The solid carrier spray apparatus of claim 10 wherein the in-line flow rate indicator is a visible ball apparatus containing a ball therein, wherein the ball is a floating ball or sinking ball which moves due to changes in movement of the liquid through the visible ball apparatus, changes position due to changes in movement of the liquid through the visible ball apparatus, or both.

12. The solid carrier sprayer apparatus of claim 1, wherein the liquid container is configured to keep the liquid contained therein in a mixed state.

13. The solid carrier sprayer apparatus of claim 12, wherein the liquid container comprises a conical bottom portion having a narrower portion and a wider portion, with the narrower portion located proximate to a bottom of the conical bottom portion.

14. The solid carrier sprayer apparatus of claim 13, further comprising an agitator located in the liquid container and configured to agitate liquid in the conical bottom portion of the liquid container.

15. The solid carrier sprayer apparatus of claim 12, wherein the liquid container comprises a sump coupled thereto proximate to a bottom, and an agitator located in the sump and configured to agitate liquid therein.

16. The solid carrier sprayer apparatus of claim 12, wherein the liquid container is a first liquid container and the apparatus further comprises a second liquid container less than one-third the size of the first liquid container.

17. The solid carrier sprayer apparatus of claim 16, wherein the second liquid container is configured to be selectively coupled to the liquid application apparatus, such that liquid from the second liquid container can be selectively applied to the received solid carrier.

18. The solid carrier sprayer apparatus of claim 16, wherein the second liquid container is configured to hold water to clean the solid carrier sprayer apparatus and attached hoses and nozzles, with a hose connected thereto.

19. The solid carrier sprayer apparatus of claim 16, further comprising a drain apparatus configurable to selectively drain the first liquid container or the second liquid container.

20. The solid carrier sprayer apparatus of claim 16, further comprising a liquid container selector apparatus configured to selectively couple the sprayer apparatus to the first liquid container or the second liquid container.

21. The solid carrier sprayer apparatus of claim 16, further comprising an agitator selector apparatus configured to selectively agitate the first liquid container or the second liquid container.

22. The solid carrier spray apparatus of claim 16, wherein the first liquid container is sized to hold liquid capable of treating at least three acres of ground.

23. The solid carrier sprayer apparatus of claim 1 wherein the solid carrier spreading apparatus comprises the solid carrier container and a conveyer.

24. The solid carrier sprayer apparatus of claim 1 further comprising a foam marker apparatus configured to deposit a visible foam trail marking the distributed solid carrier.

25. The solid carrier sprayer apparatus of claim 24, wherein the foam marker apparatus is configured to mark at least one edge, mark a center of the distributed solid carrier, or both.

26. The solid carrier sprayer apparatus of claim 1 further comprising a rate controller configured to control a rate of the liquid sprayed onto the solid carrier, a rate of solid carrier exiting a solid carrier container, a rate of sprayed solid carrier distributed over the area of ground, or a combination thereof.

27. The solid carrier sprayer apparatus of claim 26 wherein the rate controller comprises a preset parameter for a liquid flow rate from the liquid container, a solid carrier flow rate from the solid carrier container, a solid carrier distribution rate over the area of ground, or a combination thereof.

28. The solid carrier sprayer apparatus of claim 27 connected to a forward moving vehicle having wheels, wherein the distribution rate is controlled by adjusting a rate of rotation of the wheels, adjusting turret spray nozzle sizes, adjusting turret spray nozzle number, adjusting pressure of the liquid, or a combination thereof.

29. The method of claim 28, wherein the foam marker apparatus is configured to mark at least one of an edge of the distributed sprayed solid carrier.

30. The method of claim 29 further comprising mixing the liquid in the first liquid container.

31. The method of claim 30, wherein the container comprises a conical bottom portion and the mixing step comprises agitating the liquid with an agitator located in the conical bottom portion of the first liquid container.

32. The method of claim 30, wherein the mixing step comprises agitating the liquid with an agitator located in a sump, wherein the sump is coupled to the first liquid container proximate to a bottom of the first liquid container.

33. The method of claim 30, further comprising selectively coupling a second liquid container to the liquid application apparatus, such that liquid from the second liquid container can be selectively applied to the received solid carrier.

34. The solid carrier spray apparatus of claim 1 wherein the solid carrier spreading apparatus comprises a drop spreader or a spinner.

35. The solid carrier sprayer apparatus of claim 1 wherein the liquid further comprises an insecticide.

36. A method of operating a solid carrier sprayer comprising:
receiving solid carrier from a solid carrier container;
receiving liquid from a liquid container;
spraying the received liquid over the received solid carrier to form a sprayed solid carrier; and
spreading the sprayed solid carrier over an area of ground with a solid carrier spreading apparatus to form a distributed sprayed solid carrier, wherein the apparatus is connected to a forward moving vehicle and a user activates the solid sprayer apparatus after the forward moving vehicle is in motion.

37. The method of claim 36, wherein the spraying step comprises selectively spraying the solid carrier with the liquid using two or more independently controllable spray nozzles configured to spray only a portion of the solid carrier with the liquid.

38. The method of claim 36, further comprising rotating a turret to select which of using two or more spray nozzles on the turret is coupled to receive and spray the liquid.

39. The method of claim 38 wherein said turret nozzles have different rates of flow at a same received liquid pressure.

40. The method of claim 36, further comprising indicating flow of the liquid from the liquid container via at least one in-line flow rate indicator coupled between the liquid container and the liquid application apparatus.

41. The method of claim 40 wherein the in-line flow rate indicator is a visible ball apparatus containing a ball therein, wherein the ball is a floating ball which moves due to changes in movement of the liquid through the visible apparatus or a sinking ball which changes position due to changes in movement of the liquid through the visible ball apparatus, or both a floating ball and a sinking ball.

42. The method of claim 36 further comprising depositing a visible foam trail to mark the distributed sprayed solid carrier.

43. The method of claim 36 wherein the liquid is selected from a humate, fertilizer, fungicide, antifungal, insecticide, nematicide, weed killer, plant growth regulator, supplement, oil, soil wetting agent, herbicide, and combinations thereof, and the solid carrier is selected from sand, peat, organic matter, soil, and combinations thereof.

44. The method of claim 36 wherein the solid carrier apparatus also contains a solid capable of being sprayed, the solid comprising a fertilizer, insecticide, a supplement, or a combination thereof.

45. The method of claim 36 comprising adjusting an amount of distributed sprayed solid carrier deposited in a given location by adjusting the turret nozzle size, by adjusting the speed of the forward moving vehicle, or both.

46. A solid carrier sprayer apparatus, comprising:
a solid carrier container;
a liquid container;
a solid carrier spreading apparatus coupled to the solid carrier container and configured to distribute a solid carrier received from the solid carrier container over an area of ground; and
a liquid application apparatus comprising one or more spray nozzles coupled to the liquid container and configured to spray a liquid received from the liquid container over the received solid carrier, such that the liquid is sprayed over the received solid carrier before the solid carrier is distributed over the area of ground, wherein the apparatus is connected to a forward moving vehicle.

* * * * *

UNITED STATES PATENT AND TRADEMARK OFFICE
CERTIFICATE OF CORRECTION

PATENT NO. : 9,549,499 B2  
APPLICATION NO. : 14/101723  
DATED : January 24, 2017  
INVENTOR(S) : Detweiler et al.

Page 1 of 1

It is certified that error appears in the above-identified patent and that said Letters Patent is hereby corrected as shown below:

In the Specification

Column 9/Line 25: Error reads as "enable" and should read as "enables"

Signed and Sealed this
Sixteenth Day of May, 2017

Michelle K. Lee
*Director of the United States Patent and Trademark Office*